(12) United States Patent
Oosake

(10) Patent No.: US 12,283,367 B2
(45) Date of Patent: Apr. 22, 2025

(54) MEDICAL IMAGE PROCESSING APPARATUS, MEDICAL IMAGE PROCESSING METHOD, AND PROGRAM

(71) Applicant: FUJIFILM Corporation, Tokyo (JP)

(72) Inventor: Masaaki Oosake, Kanagawa (JP)

(73) Assignee: FUJIFILM Corporation, Tokyo (JP)

( * ) Notice: Subject to any disclaimer, the term of this patent is extended or adjusted under 35 U.S.C. 154(b) by 442 days.

(21) Appl. No.: 17/752,403

(22) Filed: May 24, 2022

(65) Prior Publication Data

US 2022/0285010 A1    Sep. 8, 2022

Related U.S. Application Data

(63) Continuation of application No. PCT/JP2020/047179, filed on Dec. 17, 2020.

(30) Foreign Application Priority Data

Dec. 26, 2019  (JP) ................. 2019-236673

(51) Int. Cl.
  *G16H 30/40*   (2018.01)
  *A61B 1/00*    (2006.01)
  *G16H 30/20*   (2018.01)

(52) U.S. Cl.
  CPC ....... *G16H 30/40* (2018.01); *A61B 1/000095* (2022.02); *G16H 30/20* (2018.01)

(58) Field of Classification Search
  CPC .. G16H 30/40; G16H 30/20; A61B 1/000095; A61B 1/000096;

(Continued)

(56) References Cited

U.S. PATENT DOCUMENTS

2008/0039692 A1   2/2008  Hirakawa
2019/0298159 A1  10/2019  Kimura et al.
2021/0042925 A1   2/2021  Usuda

FOREIGN PATENT DOCUMENTS

JP  2006288878 A  * 10/2006  ......... A61B 1/00009
JP  2007-319478 A   12/2007
(Continued)

OTHER PUBLICATIONS

The extended European search report issued by the European Patent Office on Jan. 11, 2023, which corresponds to European Patent Application No. 20905063.2-1126 and is related to U.S. Appl. No. 17/752,403.

(Continued)

*Primary Examiner* — Zhitong Chen
(74) *Attorney, Agent, or Firm* — Studebaker Brackett PLLC

(57) ABSTRACT

Provided is a medical image processing apparatus, a medical image processing method, and a program that are capable of reducing a gap between recognition by a recognizer and recognition by a user. The medical image processing apparatus is a medical image processing apparatus including a processor (210), a memory (207), and a monitor (400). The processor (204) is configured to sequentially acquire a plurality of medical images in a chronological manner; recognize, on the basis of the acquired medical images, a specific scene in the medical images; acquire a recognition frequency of the recognized specific scene; and cause the monitor to display, in accordance with the recognition frequency, a notification indication that changes in two or more stages and that indicates a degree of recognition.

15 Claims, 14 Drawing Sheets

(58) Field of Classification Search
CPC ..... A61B 1/000094; A61B 1/043; A61B 1/05; A61B 1/0638; A61B 1/0669; A61B 1/07; A61B 1/0005
See application file for complete search history.

(56) References Cited

FOREIGN PATENT DOCUMENTS

| | | | | |
|---|---|---|---|---|
| JP | 2008061704 A | * | 3/2008 | ......... A61B 1/00045 |
| JP | 2011-008676 A | | 1/2011 | |
| JP | 2011-087793 A | | 5/2011 | |
| JP | 2012-070938 A | | 4/2012 | |
| JP | 2015-112429 A | | 6/2015 | |
| JP | 2019-216948 A | | 12/2019 | |
| WO | 2019/220848 A1 | | 11/2019 | |

OTHER PUBLICATIONS

"Notice of Reasons for Refusal" Office Action issued in JP 2021-567366; mailed by the Japanese Patent Office on Jul. 11, 2023.
International Search Report issued in PCT/JP2020/047179; mailed Feb. 22, 2021.
International Preliminary Report On Patentability and Written Opinion issued in PCT/JP2020/047179; issued Jun. 28, 2022.
An Office Action; "Notice of Reasons for Refusal," mailed by the Japanese Patent Office on Jan. 30, 2024, which corresponds to Japanese Patent Application No. 2021-567366 and is related to U.S. Appl. No. 17/752,403; with English language translation.
"Decision of Refusal" Office Action issued in JP 2021-567366; mailed by the Japanese Patent Office on Sep. 3, 2024.
An Office Action; mailed by the China National Intellectual Property Administration of the People's Republic of China On Nov. 11, 2024, which corresponds to Chinese Patent Application No. 202080086065.6 and is related to U.S. Appl. No. 17/752,403.

* cited by examiner

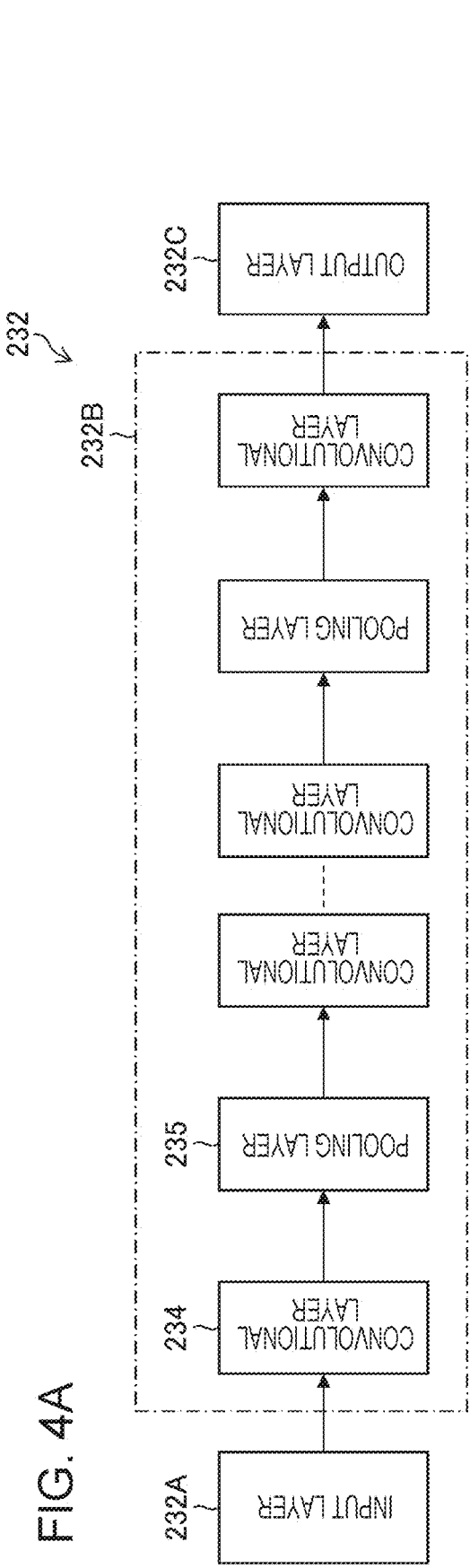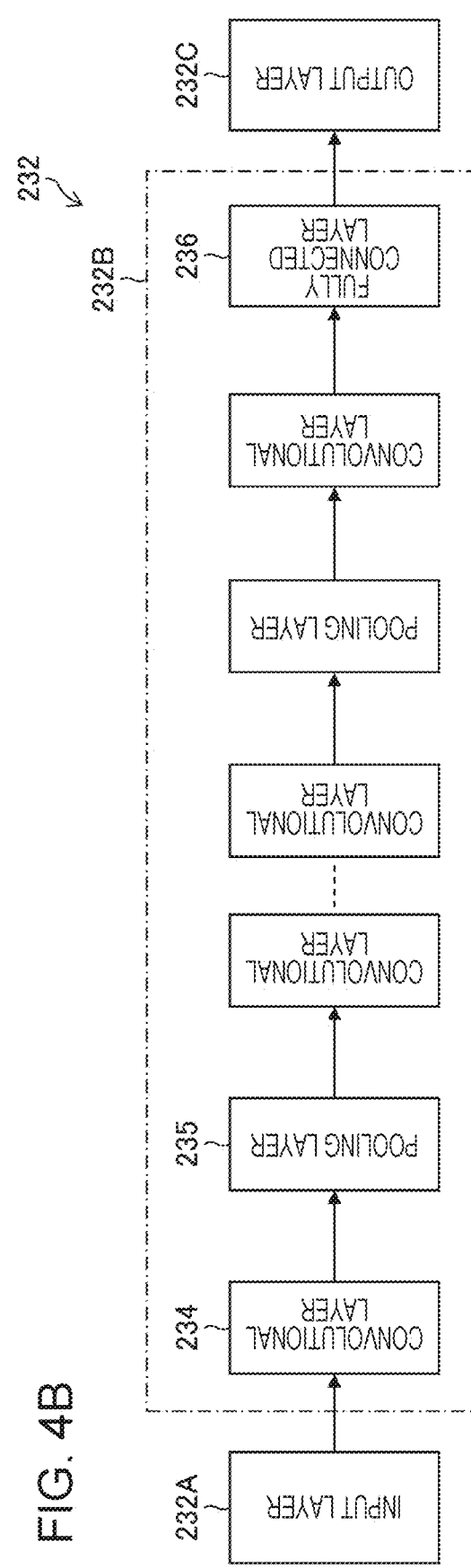

MEDICAL IMAGE PROCESSING APPARATUS, MEDICAL IMAGE PROCESSING METHOD, AND PROGRAM

CROSS-REFERENCE TO RELATED APPLICATIONS

The present application is a Continuation of PCT International Application No. PCT/JP2020/047179 filed on Dec. 17, 2020 claiming priority under 35 U.S.C § 119(a) to Japanese Patent Application No. 2019-236673 filed on Dec. 26, 2019. Each of the above applications is hereby expressly incorporated by reference, in its entirety, into the present application.

BACKGROUND OF THE INVENTION

1. Field of the Invention

The present invention relates to a medical image processing apparatus, a medical image processing method, and a program.

2. Description of the Related Art

Diagnosis and examination using an endoscope apparatus are performed by a doctor observing an endoscopic image acquired by the endoscope apparatus and displayed on a monitor.

As described in JP2011-87793A, there has been known a technique of processing an endoscopic image to estimate a lesion portion and displaying the lesion portion on a monitor with a mark superimposed thereon, thereby assisting a doctor in observing.

SUMMARY OF THE INVENTION

Furthermore, in recent years, deep learning has enabled a target in an image to be automatically recognized with high accuracy. One example of applying deep learning to an endoscope apparatus is use of a recognizer created by deep learning. Specifically, a specific scene in an endoscopic image is automatically recognized by a recognizer created by deep learning, and the recognized specific scene is presented to a user (a doctor or the like) to notify the user that the specific scene has been observed.

However, a gap may occur between recognizing of the specific scene by the recognizer and actually observing of the specific scene by the user. For example, even in a case where a specific scene is instantaneously photographed when an endoscope is quickly moved, the recognizer may recognize the specific scene. In this case, the user is notified that the specific scene has been recognized. In the case where the specific scene is instantaneously photographed, however, the user does not observe the specific scene. In this way, a gap may occur between recognizing of the specific scene by the recognizer and actually observing of the specific scene by the user.

Furthermore, because the recognizer notifies the user that the specific scene has been observed, there is a possibility that the user may wrongly recognize, on viewing a notification indication, that the specific scene has been observed, although the user has not actually observed the specific scene.

The present invention has been made in view of these circumstances, and an object of the present invention is to provide a medical image processing apparatus, a medical image processing method, and a program that are capable of reducing a gap between recognition by a recognizer and recognition by a user.

A medical image processing apparatus according to an aspect of the present invention for achieving the above object is a medical image processing apparatus including a processor. The processor is configured to sequentially acquire a plurality of medical images in a chronological manner; recognize, on the basis of the acquired medical images, a specific scene in the medical images; acquire a recognition frequency of the recognized specific scene; and cause a monitor to display, in accordance with the recognition frequency, a notification indication that changes in two or more stages and that indicates a degree of recognition.

According to this aspect, a notification indication that changes in two or more stages and that indicates a degree of recognition is displayed on the monitor in accordance with the recognition frequency of the specific scene in the medical images. This makes it possible to notify a user of the recognition frequency of the specific scene in the processor and reduce a gap between observation of the specific scene by the user and recognition of the specific scene by the processor.

Preferably, the processor is configured to cause the monitor to display the notification indication in a color that varies according to the recognition frequency.

Preferably, the processor is configured to cause the monitor to display the notification indication with a line type that varies according to the recognition frequency.

Preferably, the processor is configured to cause the monitor to display the notification indication at a degree of blur that varies according to the recognition frequency.

Preferably, the processor is configured to acquire the recognition frequency on the basis of the number of the medical images of the recognized specific scene.

Preferably, the processor is configured to acquire the recognition frequency on the basis of the number of the medical images that are chronologically consecutive of the recognized specific scene.

Preferably, the processor is configured to calculate a feature quantity of the medical images of the specific scene and classify the medical images on the basis of the feature quantity of the specific scene, to recognize the specific scene.

Preferably, the processor is configured to calculate a feature quantity of the medical images of the specific scene and recognize the specific scene on the basis of a similarity between the feature quantity and the medical images.

Preferably, the processor is configured to, in a case where the recognition frequency is higher than or equal to a first threshold value, switch the notification indication from an initial indication to a first indication and cause the monitor to display the first indication.

Preferably, the processor is configured to, in a case where the recognition frequency is higher than or equal to a second threshold value larger than the first threshold value, switch the notification indication from the first indication to a second indication and cause the monitor to display the second indication.

Preferably, the processor is configured to cause the monitor to display a plurality of reference images each having one of a plurality of the specific scenes, and is configured to provide the first indication and the second indication.

Preferably, the processor is configured to cause the monitor to display a model image including areas corresponding to a plurality of the specific scenes, and is configured to provide the first indication and the second indication, with the model image being associated with the specific scenes that have been recognized.

Preferably, the processor is configured to cause the monitor to display the notification indication such that the notification indication is superimposed on the model image, with positions at which the specific scenes have been recognized being associated with positions on the model image.

Preferably, the processor is configured to, in a case where the specific scene is not yet recognized, cause the monitor to display an initial indication different from the notification indication.

A medical image processing method according to another aspect of the present invention includes a medical image acquisition step of sequentially acquiring a plurality of medical images in a chronological manner; a specific scene recognition step of recognizing, on the basis of the acquired medical images, a specific scene in the medical images; a frequency acquisition step of acquiring a recognition frequency of the specific scene recognized in the specific scene recognition step; and a display control step of causing a monitor to display, in accordance with the recognition frequency, a notification indication that changes in two or more stages and that indicates a degree of recognition.

A program according to another aspect of the present invention causes a computer to execute a medical image processing method including a medical image acquisition step of sequentially acquiring a plurality of medical images in a chronological manner; a specific scene recognition step of recognizing, on the basis of the acquired medical images, a specific scene in the medical images; a frequency acquisition step of acquiring a recognition frequency of the specific scene recognized in the specific scene recognition step; and a display control step of causing a monitor to display, in accordance with the recognition frequency, a notification indication that changes in two or more stages and that indicates a degree of recognition.

According to the present invention, a gap between recognition by a recognizer and recognition by a user can be reduced.

BRIEF DESCRIPTION OF THE DRAWINGS

FIGS. 4A and 4B are diagrams illustrating configurations of a CNN;

DESCRIPTION OF THE PREFERRED EMBODIMENTS

Hereinafter, preferred embodiments of a medical image processing apparatus, a medical image processing method, and a program according to the present invention will be described with reference to the attached drawings.

Configuration of Endoscope System

Figure 1:
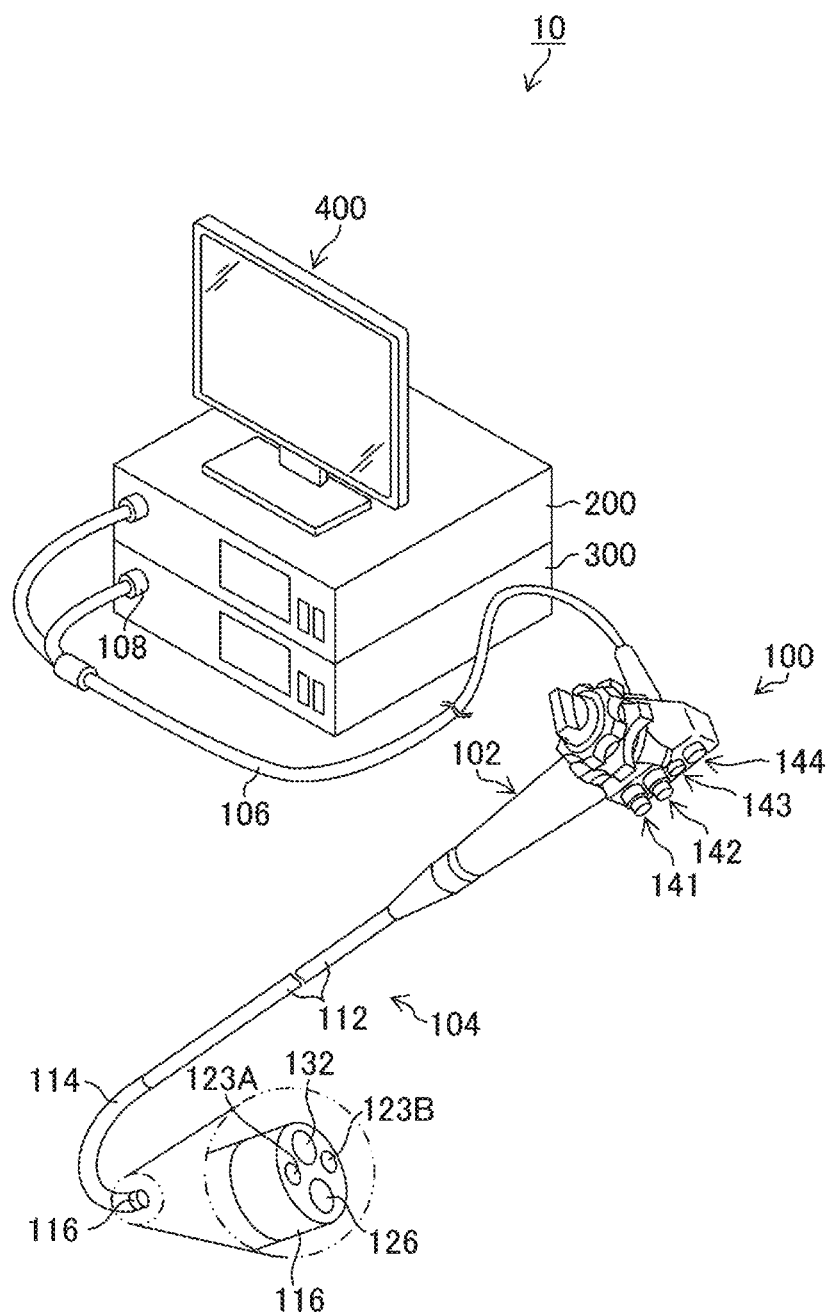
FIG. 1 is an external appearance diagram of an endoscope system.
Figure 2:
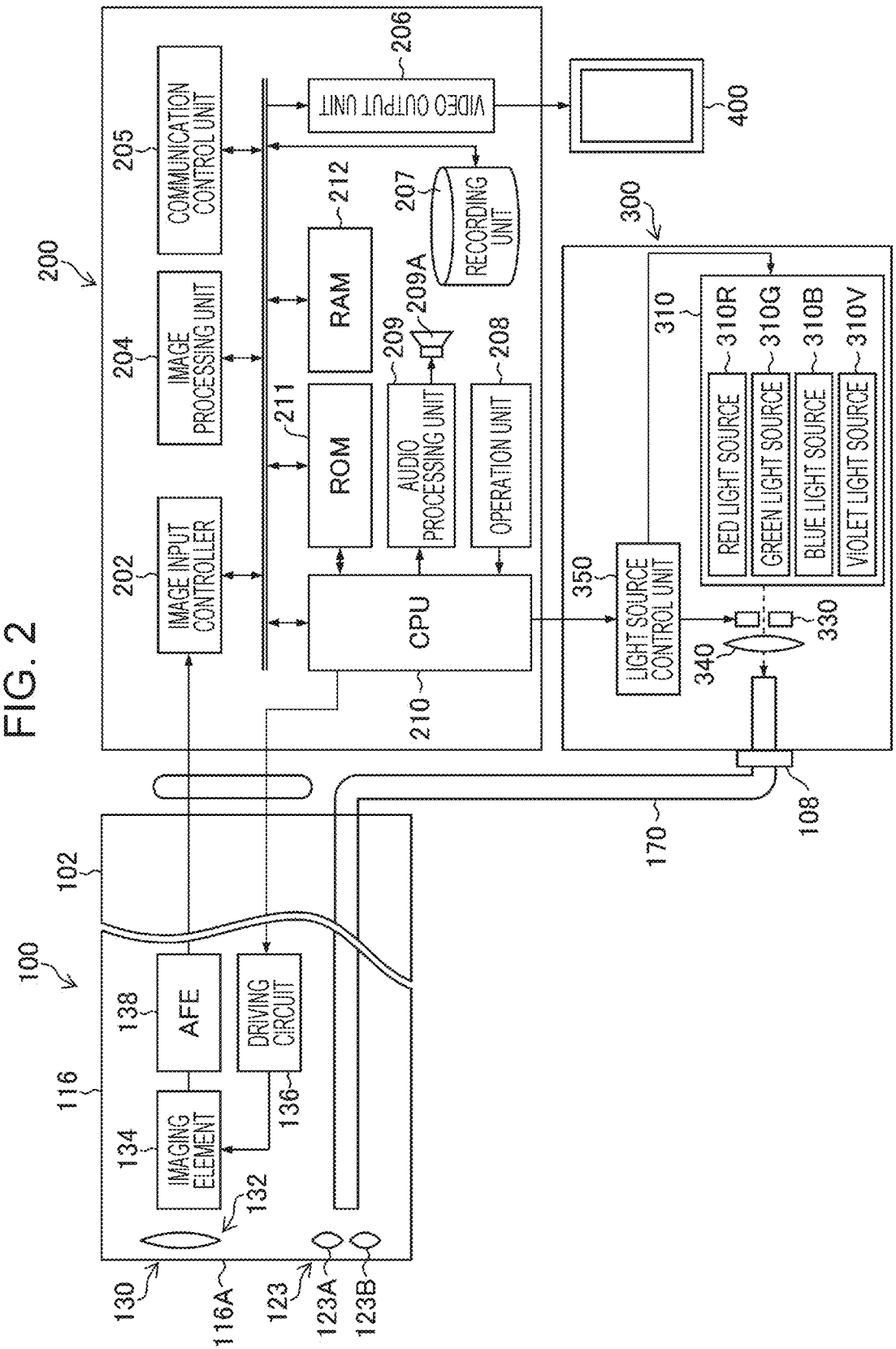
FIG. 2 is a block diagram illustrating the configuration of a main part of the endoscope system.

FIG. 1 is an external appearance diagram of an endoscope system 10, and FIG. 2 is a block diagram illustrating the configuration of a main part of the endoscope system 10. As illustrated in FIGS. 1 and 2, the endoscope system 10 is constituted by an endoscope 100, an endoscope processor apparatus 200, a light source apparatus 300, and a monitor 400. The endoscope processor apparatus 200 has the medical image processing apparatus of the present invention mounted therein.

Configuration of Endoscope

The endoscope 100 includes a handheld operation section 102 and an insertion section 104 that communicates with the handheld operation section 102. An operator (a user) operates the handheld operation section 102 while grasping it and inserts the insertion section 104 into a body of a subject (a living body) to perform observation. The handheld operation section 102 is provided with an air/water supply button 141, a suction button 142, a function button 143 to which various functions are allocated, and an imaging button 144 for receiving an imaging instruction operation (a still image, a moving image). The insertion section 104 is constituted by a soft part 112, a bending part 114, and a tip rigid part 116, which are arranged in this order from the handheld operation section 102 side. That is, the bending part 114 is connected to a base end side of the tip rigid part 116, and the soft part 112 is connected to a base end side of the bending part 114. The handheld operation section 102 is connected to a base end side of the insertion section 104. The user is able to change the orientation of the tip rigid part 116 in an up, down, left, or right direction by causing the bending part 114 to bend by operating the handheld operation section 102. The tip rigid part 116 is provided with an imaging optical system 130, an illumination unit 123, a forceps port 126, and so forth (see FIGS. 1 and 2).

During observation and treatment, an operation of an operation unit 208 (see FIG. 2) enables white light and/or narrow-band light (one or more of red narrow-band light, green narrow-band light, blue narrow-band light, and violet narrow-band light) to be radiated from illumination lenses 123A and 123B of the illumination unit 123. In addition, an operation of the air/water supply button 141 enables washing water to be ejected from a water supply nozzle that is not illustrated, so that an imaging lens 132 of the imaging optical system 130 and the illumination lenses 123A and 123B can be washed. The forceps port 126 opening in the tip rigid part 116 communicates with a pipe line that is not illustrated, so that a treatment tool that is not illustrated and is for extirpating a tumor or the like can be inserted into the pipe line and necessary treatment can be given to a subject by moving the treatment tool forward or backward as appropriate.

As illustrated in FIG. 1 and FIG. 2, the imaging lens 132 is disposed on a distal-end-side surface 116A of the tip rigid part 116. An imaging element 134 of a complementary metal-oxide semiconductor (CMOS) type, a driving circuit 136, and an analog front end (AFE) 138 are disposed behind the imaging lens 132, and these elements output an image signal. The imaging element 134 is a color imaging element and includes a plurality of pixels constituted by a plurality of light-receiving elements arranged in a matrix (arranged two-dimensionally) in a specific pattern arrangement (Bayer arrangement, X-Trans (registered trademark) arrangement, honeycomb arrangement, or the like). Each pixel of the imaging element 134 includes a microlens, a red (R), green (G), or blue (B) color filter, and a photoelectric conversion unit (a photodiode or the like). The imaging optical system 130 is capable of generating a color image from pixel signals of three colors, red, green, and blue, and is also capable of generating an image from pixel signals of any one or two colors among red, green, and blue. The imaging element 134 may be of a charge coupled device (CCD) type. Each pixel of the imaging element 134 may further include a violet color filter corresponding to a violet light source 310V and/or an infrared filter corresponding to an infrared light source.

An optical image of a subject is formed on a light-receiving surface (an imaging surface) of the imaging element 134 by the imaging lens 132, converted into an electric signal, output to the endoscope processor apparatus 200 through a signal cable that is not illustrated, and converted into a video signal. Accordingly, an endoscopic image (medical image) of the subject is displayed on the monitor 400, which is connected to the endoscope processor apparatus 200.

The illumination lenses 123A and 123B of the illumination unit 123 are provided next to the imaging lens 132 on the distal-end-side surface 116A of the tip rigid part 116. An emission end of a light guide 170, which will be described below, is disposed behind the illumination lenses 123A and 123B. The light guide 170 extends through the insertion section 104, the handheld operation section 102, and a universal cable 106, and an incidence end of the light guide 170 is located in a light guide connector 108.

A user performs imaging at a determined frame rate while inserting or removing the endoscope 100 having the above-described configuration into or from a living body as a subject, thereby being capable of sequentially capturing chronological endoscopic images of the inside of the living body.

Configuration of Light Source Apparatus

As illustrated in FIG. 2, the light source apparatus 300 is constituted by a light source 310 for illumination, a diaphragm 330, a condenser lens 340, a light source control unit 350, and so forth, and causes observation light to enter the light guide 170. The light source 310 includes a red light source 310R, a green light source 310G, a blue light source 310B, and the violet light source 310V that radiate red narrow-band light, green narrow-band light, blue narrow-band light, and violet narrow-band light, respectively, and is capable of radiating red narrow-band light, green narrow-band light, blue narrow-band light, and violet narrow-band light. The illuminance of observation light from the light source 310 is controlled by the light source control unit 350, which is capable of changing (increasing or decreasing) the illuminance of observation light or stopping illumination as necessary.

The light source 310 is capable of emitting red narrow-band light, green narrow-band light, blue narrow-band light, and violet narrow-band light in any combination. For example, the light source 310 is capable of simultaneously emitting red narrow-band light, green narrow-band light, blue narrow-band light, and violet narrow-band light to radiate white light (normal light) as observation light, and is also capable of emitting any one or two of red narrow-band light, green narrow-band light, blue narrow-band light, and violet narrow-band light to radiate narrow-band light (special light). The light source 310 may further include an infrared light source that radiates infrared light (an example of narrow-band light). Alternatively, with use of a light source that radiates white light and a filter that allows white light and each narrow-band light to pass therethrough, white light or narrow-band light may be radiated as observation light.

Wavelength Range of Light Source

The light source 310 may be a light source that generates light in a white range or light in a plurality of wavelength ranges as the light in the white range, or may be a light source that generates light in a specific wavelength range narrower than the white wavelength range. The specific wavelength range may be a blue range or green range in a visible range, or may be a red range in the visible range. In a case where the specific wavelength range is the blue range or green range in the visible range, the specific wavelength range may include a wavelength range of 390 nm or more and 450 nm or less or a wavelength range of 530 nm or more and 550 nm or less, and the light in the specific wavelength range may have a peak wavelength in the wavelength range of 390 nm or more and 450 nm or less or the wavelength range of 530 nm or more and 550 nm or less. In a case where the specific wavelength range is the red range in the visible range, the specific wavelength range may include a wavelength range of 585 nm or more and 615 nm or less or a wavelength range of 610 nm or more and 730 nm or less, and the light in the specific wavelength range may have a peak wavelength in the wavelength range of 585 nm or more and 615 nm or less or the wavelength range of 610 nm or more and 730 nm or less.

The above-described specific wavelength range may include a wavelength range in which a light absorption coefficient is different between oxyhemoglobin and deoxyhemoglobin, and the light in the specific wavelength range may have a peak wavelength in the wavelength range in which the light absorption coefficient is different between oxyhemoglobin and deoxyhemoglobin. In this case, the specific wavelength range may include a wavelength range of 400±10 nm, a wavelength range of 440±10 nm, a wavelength range of 470±10 nm, or a wavelength range of 600 nm or more and 750 nm or less, and the light in the specific wavelength range may have a peak wavelength in the wavelength range of 400±10 nm, the wavelength range of 440±10 nm, the wavelength range of 470±10 nm, or the wavelength range of 600 nm or more and 750 nm or less.

The wavelength range of the light generated by the light source 310 may include a wavelength range of 790 nm or more and 820 nm or less or a wavelength range of 905 nm or more and 970 nm or less, and the light generated by the light source 310 may have a peak wavelength in the wavelength range of 790 nm or more and 820 nm or less or the wavelength range of 905 nm or more and 970 nm or less.

Alternatively, the light source 310 may include a light source that radiates excitation light whose peak is 390 nm or more and 470 nm or less. In this case, an endoscopic image having information about fluorescence emitted by a fluorescent substance in a subject (a living body) can be acquired. In the case of acquiring a fluorescence image, a pigment for a fluorescence method (fluorescein, acridine orange, or the like) may be used.

It is preferable that the type of the light source 310 (a laser light source, a xenon light source, a light-emitting diode (LED) light source, or the like), the wavelength of the light source 310, the presence or absence of a filter for the light source 310, and so forth be determined in accordance with the type, area, purpose of observation, or the like of a photographic subject. It is also preferable that, during observation, the wavelengths of observation light be combined and/or switched in accordance with the type, area, purpose of observation, or the like of a photographic subject. In the case of switching the wavelength, for example, a disc-shaped filter (a rotary color filter) that is disposed in front of the light source and that is provided with a filter for transmitting or blocking light of a specific wavelength may be rotated to switch the wavelength of light to be radiated.

The imaging element used to carry out the present invention is not limited to a color imaging element in which color filters are disposed for the individual pixels, such as the imaging element 134, and may be a monochrome imaging element. In the case of using a monochrome imaging element, imaging can be performed in a frame sequential (color sequential) manner by sequentially switching the wavelength of observation light. For example, the wavelength of outgoing observation light may be sequentially switched among violet, blue, green, and red, or wide-band light (white light) may be radiated and the wavelength of outgoing observation light may be switched by using a rotary color filter (red, green, blue, violet, and the like). Alternatively, one or a plurality of types of narrow-band light (green, blue, violet, and the like) may be radiated and the wavelength of outgoing observation light may be switched by using a rotary color filter (green, blue, violet, and the like). The narrow-band light may be infrared light of two or more different wavelengths (first narrow-band light and second narrow-band light).

As a result of connecting the light guide connector 108 (see FIGS. 1 and 2) to the light source apparatus 300, observation light radiated by the light source apparatus 300 is transmitted through the light guide 170 to the illumination lenses 123A and 123B and is radiated from the illumination lenses 123A and 123B to an observation range.

Configuration of Endoscope Processor Apparatus

The configuration of the endoscope processor apparatus 200 will be described with reference to FIG. 2. In the endoscope processor apparatus 200, an image input controller 202 receives an image signal output from the endoscope 100, an image processing unit 204 performs necessary image processing thereon, and a video output unit 206 outputs a resulting image signal. Accordingly, an endoscopic image is displayed on the monitor 400. These processing operations are performed under control by a central processing unit (CPU) 210. The CPU 210 functions as a processor of the medical image processing apparatus. A communication control unit 205 controls communication, for acquiring a medical image, with a hospital information system (HIS), a hospital local area network (LAN), and/or an external system or network that are not illustrated.

Functions of Image Processing Unit

The image processing unit 204 is capable of performing calculation of a feature quantity of an endoscopic image, processing of emphasizing or reducing a component of a specific frequency band, and processing of emphasizing or deemphasizing a specific target (a region of interest, blood vessels at a desired depth, or the like). The image processing unit 204 may include a special-light image acquiring unit (not illustrated) that acquires a special-light image having information about a specific wavelength range on the basis of a normal-light image that is acquired by radiating light in the white range or light in a plurality of wavelength ranges as the light in the white range. In this case, a signal in the specific wavelength range can be acquired through computation based on color information of RGB (R: red, G: green, B: blue) or CMY (C: cyan, M: magenta, Y: yellow) included in the normal-light image. In addition, the image processing unit 204 may include a feature quantity image generating unit (not illustrated) that generates a feature quantity image through computation based on at least one of a normal-light image that is acquired by radiating light in the white range or light in a plurality of wavelength ranges as the light in the white range or a special-light image that is acquired by radiating light in a specific wavelength range, and may acquire and display the feature quantity image as an endoscopic image. The above-described processing is performed under control by the CPU 210.

Furthermore, the image processing unit 204 has individual functions in the medical image processing apparatus as described below.

Figure 3:
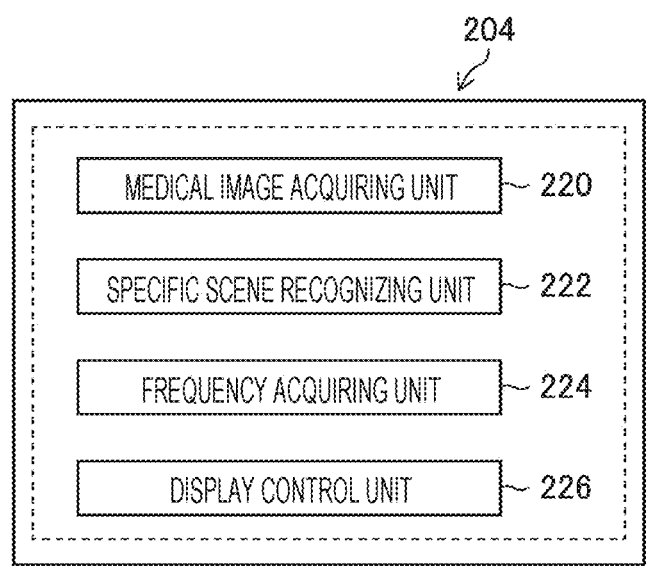
FIG. 3 is a functional block diagram of an image processing unit in a medical image processing apparatus.

FIG. 3 is a functional block diagram of the image processing unit 204 in the medical image processing apparatus. The image processing unit 204 includes a medical image acquiring unit 220, a specific scene recognizing unit 222, a frequency acquiring unit 224, and a display control unit 226.

Implementation of Functions by Various Types of Processors

The functions of the above-described units of the image processing unit 204 can be implemented by using various types of processors and a recording medium. The various types of processors include, for example, a central processing unit (CPU) which is a general-purpose processor that executes software (program) to implement various functions. Also, the various types of processors include a graphics processing unit (GPU) which is a processor dedicated to image processing, and a programmable logic device (PLD) which is a processor whose circuit configuration is changeable after manufacturing, such as a field programmable gate array (FPGA). In the case of performing learning and recognition of images as in the present invention, the configuration using a GPU is effective. Furthermore, the various types of processors include a dedicated electric circuit which is a processor having a circuit configuration designed exclusively for executing specific processing, such as an application specific integrated circuit (ASIC).

The function of each unit may be implemented by one processor or may be implemented by a plurality of processors of the same type or different types (for example, a combination of a plurality of FPGAs, a combination of a CPU and an FPGA, or a combination of a CPU and a GPU). A plurality of functions may be implemented by one processor. A first example of implementing a plurality of functions by one processor is that a combination of one or more CPUs and software constitute one processor and the one processor implements the plurality of functions, as represented by a computer. A second example is that a processor that implements the functions of an entire system by one integrated circuit (IC) chip is used, as represented by a system on chip (SoC). In this way, various functions are configured as a hardware structure by using one or more of the above-described various types of processors. Furthermore, the hardware structure of the various types of processors is, more specifically, electric circuitry formed by combining circuit elements such as semiconductor elements. The electric circuitry may be electric circuitry that implements the above-described functions by using logical disjunction, logical conjunction, logical negation, exclusive disjunction, and logical operation as a combination thereof.

When the above-described processor or electric circuitry executes the software (program), the code of the software to be executed that is readable by a computer (for example, the various types of processors or electric circuitry constituting the image processing unit 204, and/or a combination thereof) is stored in a non-transitory recording medium, such as a read only memory (ROM) 211, and the computer refers to the software. The software stored in the non-transitory recording medium includes a program for executing a method for operating the medical image processing apparatus according to the present invention and data to be used for the execution (data about acquisition of a medical image, data used to specify a notification condition and a notification mode, a parameter used in the recognizing unit, and so forth). The code may be recorded on a non-transitory recording medium, such as a magneto-optical recording device of various types or a semiconductor memory, instead of the ROM 211. In the processing using the software, a random access memory (RAM) 212 may be used as a transitory storage region, for example, and data stored in an electrically erasable and programmable read only memory (EEPROM) that is not illustrated can be referred to, for example. A recording unit 207 may be used as a "non-transitory recording medium".

The read only memory (ROM) 211 is a nonvolatile storage element (a non-transitory recording medium) and stores a computer-readable code of a program that causes the CPU 210 and/or the image processing unit 204 to execute various image processing methods. The random access memory (RAM) 212 is a storage element for temporary storage in various processing operations and can be used as a buffer when acquiring an image. An audio processing unit 209 outputs audio and sound from a speaker 209A under control by the CPU 210.

The operation unit 208 can be constituted by devices such as a keyboard and a mouse that are not illustrated. A user is able to provide an instruction to execute processing or designate a condition necessary for the execution via the operation unit 208.

The recording unit 207 stores an acquired endoscopic image. The recording unit 207 also stores a program and information for controlling the medical image processing apparatus. The recording unit 207 functions as a memory of the medical image processing apparatus.

Specific Scene Recognizing Unit Using Neural Network

The specific scene recognizing unit 222 in the above-described image processing unit 204 is constituted by a recognizer. The recognizer is constituted by using a trained model (a model trained by using an image set constituted by captured images of a living body), such as a neural network, and recognizes a specific scene. The specific scene herein includes, for example, the esophagus, duodenum, cardia, pylorus, angulus, fundus, gastric body, antrum, lesser curvature, greater curvature, and so forth. Hereinafter, a description will be given of a configuration in the case of using a convolutional neural network (CNN) as a neural network.

Example of Configuration of Recognizing Unit

FIGS. 4A and 4B are diagrams illustrating configurations of a CNN 232 (neural network). In the example illustrated in FIG. 4A, the CNN 232 has an input layer 232A, an intermediate layer 232B, and an output layer 232C. The input layer 232A receives an endoscopic image acquired by the medical image acquiring unit 220 and outputs a feature quantity. The intermediate layer 232B includes convolutional layers 234 and pooling layers 235, and receives the feature quantity output from the input layer 232A and calculates another feature quantity. These layers have a structure in which a plurality of "nodes" are connected by "edges". Weighting coefficients applied to an input image are associated with the nodes and edges and are stored in a weighting coefficient storage unit that is not illustrated. The values of the weighting coefficients change as learning progresses.

Processing in Intermediate Layer

The intermediate layer 232B calculates a feature quantity through convolutional operation and pooling processing. The convolutional operation performed in the convolutional layer 234 is processing of acquiring a feature map through convolutional operation using a filter, and plays a role in feature extraction such as edge extraction from an image. As a result of the convolutional operation using a filter, one-channel (one) "feature map" is created for one filter. The size of the "feature map" is reduced as convolution is performed in each layer in the case of being scaled down by convolution. The pooling processing performed in the pooling layer 235 is processing of reducing (or enlarging) the feature map output through the convolutional operation to create a new feature map, and plays a role in giving robustness so that the extracted feature is not affected by parallel movement or the like. The intermediate layer 232B can be constituted by one or a plurality of layers that perform these processing operations. The CNN 232 may be configured without a pooling layer 235.

The CNN 232 may include a fully connected layer 236 as in the example illustrated in FIG. 4B. The layer configuration of the CNN 232 is not limited to the configuration in which the convolutional layers 234 and the pooling layers 235 are alternately arranged, and may include a plurality of consecutive convolutional layers 234 or pooling layers 235 (for example, convolutional layers 234).

Figure 5:
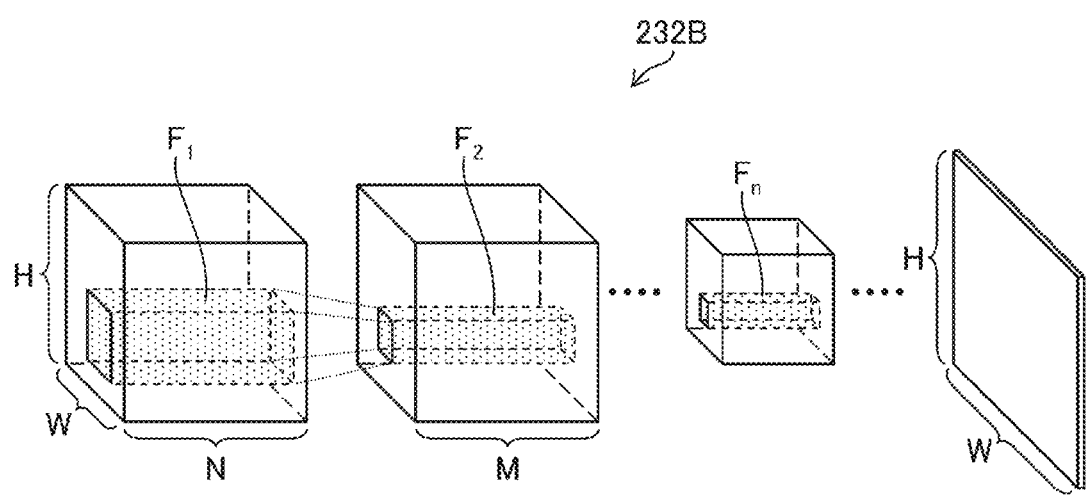
FIG. 5 is a schematic diagram illustrating an example configuration of an intermediate layer.

FIG. 5 is a schematic diagram illustrating an example configuration of the intermediate layer 232B of the CNN 232 illustrated in FIGS. 4A and 4B. In the first convolutional layer of the intermediate layer 232B, convolutional operation of an image set constituted by a plurality of endoscopic images and a filter $F_1$ is performed. The image set is constituted by N (N-channel) images each having an image size in which the height is represented by H and the width is represented by W. In the case of inputting normal-light images, the images constituting an image set are three-channel images of red (R), green (G), and blue (B). The filter $F_1$ convoluted with this image set has a filter size of $5 \times 5 \times N$ in the case of the filter having size 5 (5×5), for example, because the image set has N channels (N images). As a result of convolutional operation using the filter $F_1$, one-channel (one) "feature map" is created for one filter $F_1$. A filter $F_2$ used in the second convolutional layer has a filter size of $3 \times 3 \times M$ in the case of the filter having size 3 (3×3), for example.

As in the first convolutional layer, in the second to n-th convolutional layers, convolutional operations using filters $F_2$ to $F_n$ are performed, respectively. The size of the "feature map" in the n-th convolutional layer is smaller than the size of the "feature map" in the second convolutional layer because scaling-down is performed in the convolutional layers or pooling layers in the preceding stages.

In the layers of the intermediate layer 232B, lower-order feature extraction (extraction of edges or the like) is performed in a convolutional layer near the input side, and higher-order feature extraction (extraction of features about the shape, structure, and the like of a recognition target) is performed near the output side.

The intermediate layer 232B may include a layer for performing batch normalization in addition to the convolutional layers 234 and the pooling layers 235. Batch normalization processing is the processing of normalizing a data distribution in units of mini batches for performing learning, and plays a role in quickly performing learning, reducing dependency on an initial value, suppressing overtraining, and so forth.

The output layer 232C outputs the feature quantity calculated by the intermediate layer 232B in a form appropriate for recognizing a specific scene. The output layer 232C may include a fully connected layer.

Individual Processes of Medical Image Processing Method

Next, a medical image processing method using the medical image processing apparatus will be described. Hereinafter, a description will be given of the case of processing an endoscopic image acquired by the endoscope system 10 as a medical image, but application of the present invention is not limited thereto. For example, in the present invention, an endoscopic image acquired by another endoscope system 10 may be processed as a medical image by the medical image processing apparatus.

Figure 6:
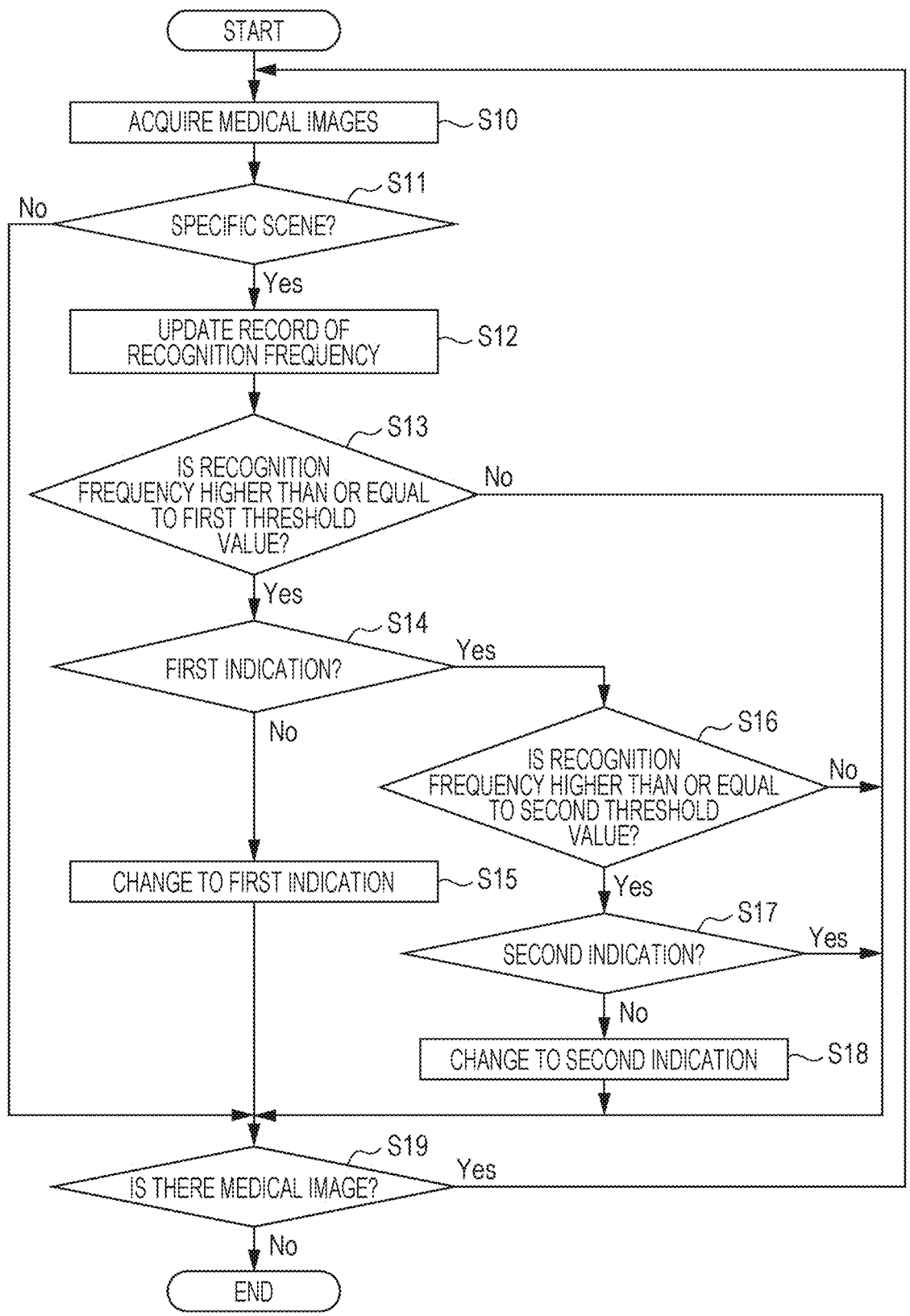
FIG. 6 is a flowchart illustrating a medical image processing method.

FIG. 6 is a flowchart illustrating a medical image processing method. Hereinafter, individual steps will be described with reference to FIG. 6.

Medical Image Acquisition Step

The medical image acquiring unit 220 sequentially acquires a plurality of medical images in a chronological manner (step S10). The medical image acquiring unit 220 may acquire medical images of a body cavity captured by the endoscope 100, or may acquire medical images of a body cavity stored in the recording unit 207.

Specific Scene Recognition Step

The specific scene recognizing unit 222 recognizes a specific scene in the acquired medical images. The specific scene recognizing unit 222 receives the medical images, inputs the medical images to the above-described CNN, and extracts a feature quantity from the medical images step by step. The specific scene recognizing unit 222 finally performs classification (for example, classification into 11 classes: esophagus; duodenum; cardia; pylorus; angulus; fundus; gastric body; antrum; lesser curvature; greater curvature; and other) by using the feature quantity, thereby recognizing a specific scene. A detailed description of this recognition method is described in the following literature: B. Zhou, A. Lapedriza, J. Xiao, A. Torralba, and A. Oliva, Learning deep features for scene recognition using places database, In Neural Information Processing Systems (NIPS), pages 487-495, 2014, 1, 4, 6, 8. In addition, the specific scene recognizing unit 222 is capable of recognizing a specific scene by comparing a finally extracted feature quantity with a feature quantity stored in advance in the recording unit 207 (for example, a feature quantity of the duodenum) and calculating a similarity. A detailed description of this recognition method is described in the following literature: FaceNet: A Unified Embedding for Face Recognition and Clustering https://arxiv.org/abs/1503.03832.

If the specific scene recognizing unit 222 is unable to recognize a specific scene in the received medical images (No in step S11) and if there is a subsequent medical image (Yes in step S19), the medical image acquiring unit 220 acquires the subsequent medical image (step S10). On the other hand, if the specific scene recognizing unit 222 is able to recognize a specific scene in the medical images (Yes in step S11), the process proceeds to a frequency acquisition step (step S12) of updating the record of a recognition frequency.

Frequency Acquisition Step

In response to the recognition of the specific scene in the medical images by the specific scene recognizing unit 222, the frequency acquiring unit 224 updates the record of a recognition frequency (step S12). For example, if the duodenum, which is a specific scene, has been recognized by the specific scene recognizing unit 222, the recognition frequency of the duodenum is updated from 0 to 1. The update of the recognition frequency may be performed in various manners. For example, the recognition frequency may be updated from 0 to 64 or the like. The update of the recognition frequency will be described in detail below.

Display Control Step

If the recognition frequency is higher than or equal to a first threshold value (Yes in step S13) and if an initial indication is displayed on the monitor 400 and a first indication, which is one of notification indications, is not yet displayed on the monitor 400 (No in step S14), the display control unit 226 changes the initial indication to the first indication (step S15).

On the other hand, if the recognition frequency is higher than or equal to the first threshold value (Yes in step S13), if the first indication is already displayed on the monitor 400 (Yes in step S14), and if the recognition frequency is higher than or equal to a second threshold value (Yes in step S16), the display control unit 226 changes the initial indication to a second indication. The first threshold value and the second threshold value are set by a user as appropriate. In this way, as a result of displaying the initial indication, the first indication, or the second indication on the monitor 400 with a step-by-step change based on the recognition frequency of the specific scene of the specific scene recognizing unit 222, the user is able to know the recognition frequency.

If the recognition frequency is lower than the first threshold value (No in step S13), if the recognition frequency is lower than the second threshold value (No in step S16), or if the second indication is already displayed on the monitor 400 (Yes in step S17), the medical image acquiring unit 220 acquires a subsequent medical image if there is the subsequent medical image (step S10).

Frequency Acquisition Step

Next, a description will be given of a frequency acquisition step performed by the frequency acquiring unit 224.

Figure 7:
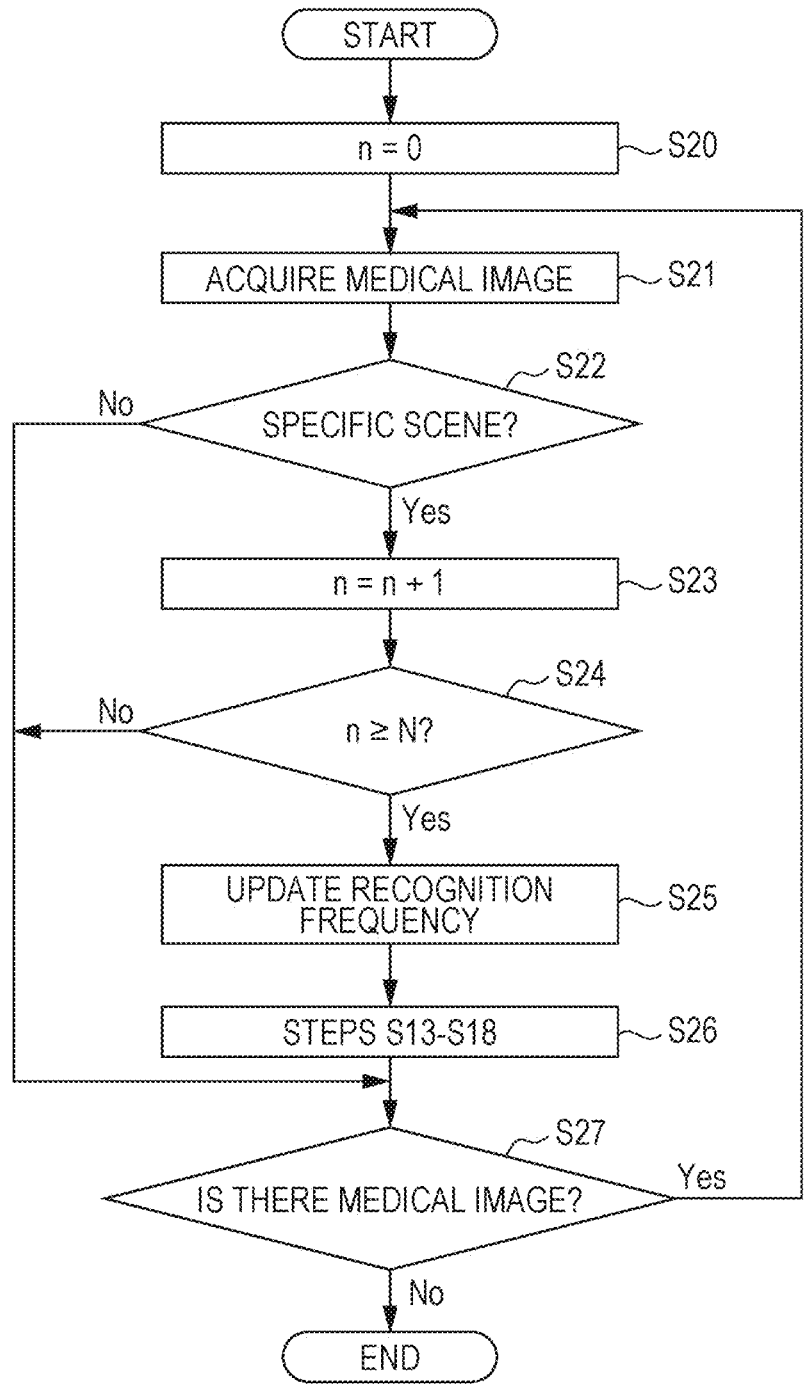
FIG. 7 is a flowchart of acquisition of a recognition frequency.

FIG. 7 is a flowchart of acquisition of a recognition frequency. With reference to FIG. 7, a description will be given of the case of updating a recognition frequency in accordance with the number of endoscopic images in which a specific scene (for example, the pylorus) has been recognized. Note that n in the figure represents the number of images in which a specific scene has been recognized, and that N is a frequency update threshold value and is set by a user as appropriate.

In an initial state, n equals 0 (step S20). The medical image acquiring unit 220 receives a medical image (step S21). If the specific scene recognizing unit 222 has recognized a specific scene in the medical image (Yes in step S22), the number of images n in which the specific scene has been recognized is updated to n+1 (step S23). If the updated number of images n is larger than or equal to the frequency threshold value N (Yes in step S24), the frequency acquiring unit 224 updates the recognition frequency (step S25). For example, if the frequency threshold value is 5 (N=5) and if the specific scene recognizing unit 222 has recognized the pylorus in five medical images, the frequency acquiring unit 224 updates the recognition frequency of the pylorus. After that, the process proceeds to the display control step described in FIG. 6 (steps S13 to S18: step S26).

If the specific scene recognizing unit 222 does not recognize a specific scene in the acquired medical image (No in step S22), if the updated number of images n is smaller than the frequency threshold value N (No in step S24), or after the display control step described in FIG. 6 (steps S13 to S18), the medical image acquiring unit 220 acquires a subsequent medical image if there is the subsequent medical image (Yes in step S27).

The specific scene recognized by the specific scene recognizing unit 222 may be one specific scene or a plurality of specific scenes. If the specific scene recognizing unit 222 recognizes a plurality of specific scenes, a frequency threshold value is set for each specific scene, and the recognition frequency is updated for each specific scene.

Notification Indication

Next, a description will be given of a notification indication on the monitor 400 provided by the display control unit 226.

Figure 8:
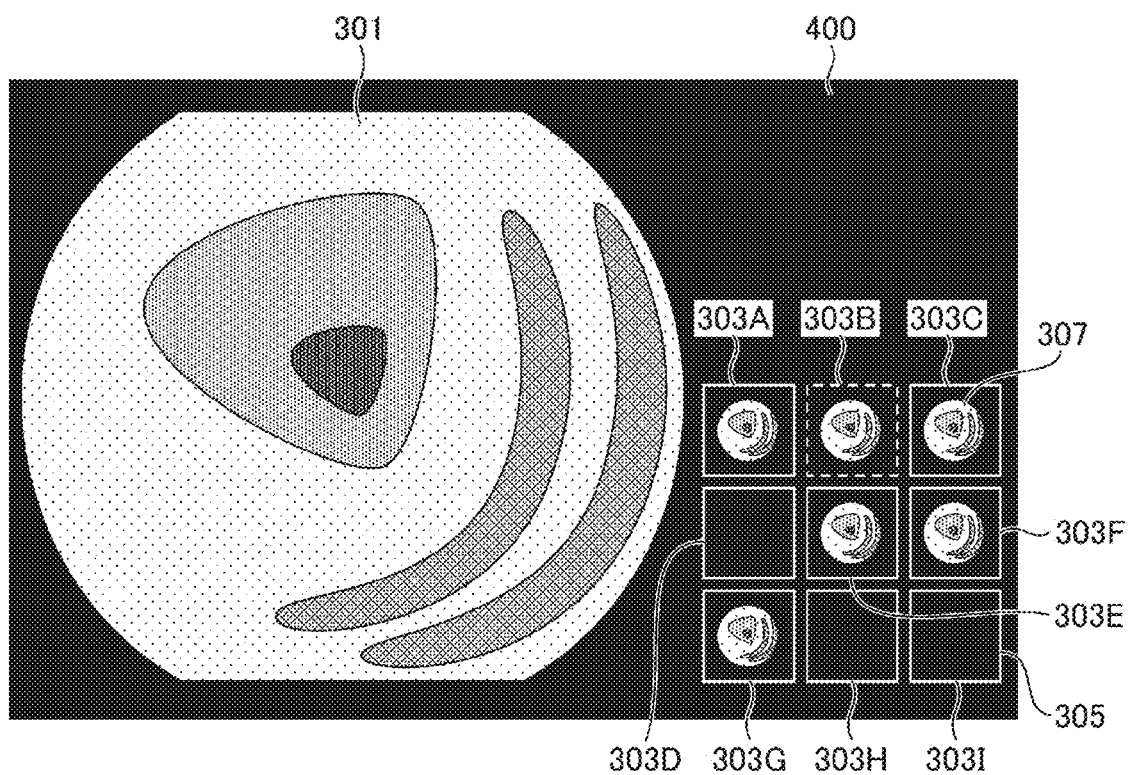
FIG. 8 is a diagram illustrating an example of a notification indication.

FIG. 8 is a diagram illustrating an example of a notification indication on the monitor 400 provided by the display control unit 226.

In the case illustrated in FIG. 8, an endoscopic image (medical image) 301 captured in real time is displayed in a main display region of the monitor 400. In a sub display region of the monitor 400, a notification indication 303 constituted by reference images is displayed.

The notification indication 303 is constituted by reference images (303A to 303I) of specific scenes 1 to 9.

In the specific scenes 4, 8, and 9 (reference signs 303D, 303H, and 303I) that are not yet recognized by the specific scene recognizing unit 222, only a frame line 305 is displayed as an initial indication. In this way, as a result of making the initial indication different from the notification indication, a user is able to know that recognition of a specific scene is not yet performed by the specific scene recognizing unit 222. On the other hand, in the specific scenes 1 to 3, 5, 6, and 7 (reference signs 303A, 303B, 303C, 303E, 303F, and 303G), the recognition frequency is higher than or equal to the first threshold value, and the first indication (a reference image 307 of the specific scene) is displayed. In the specific scene 2, the recognition frequency is higher than or equal to the second threshold value, and the second indication (the line type of the frame line 305 has been changed from a solid line to a broken line) is displayed.

As described above, in the present embodiment, a notification indication is displayed on the monitor 400 by being switched in accordance with the recognition frequency of a specific scene in a medical image, and thus a user is able to know the recognition frequency of the specific scene in the medical image processing apparatus (specific scene recognizing unit 222). Thus, the present embodiment is capable of reducing a gap between recognition by the medical image processing apparatus (specific scene recognizing unit 222) and recognition by the user.

Next, modifications of the above-described embodiment will be described.

Modification of Individual Processes of Medical Image Processing Method

A modification of individual processes of the medical image processing method will be described. In the above embodiment, a description has been given of the case where the first indication and the second indication are displayed on the monitor 400. In the present modification, a description will be given of a case where a notification indication is provided on the monitor 400 by changing it to a third or more indication.

Figure 9:
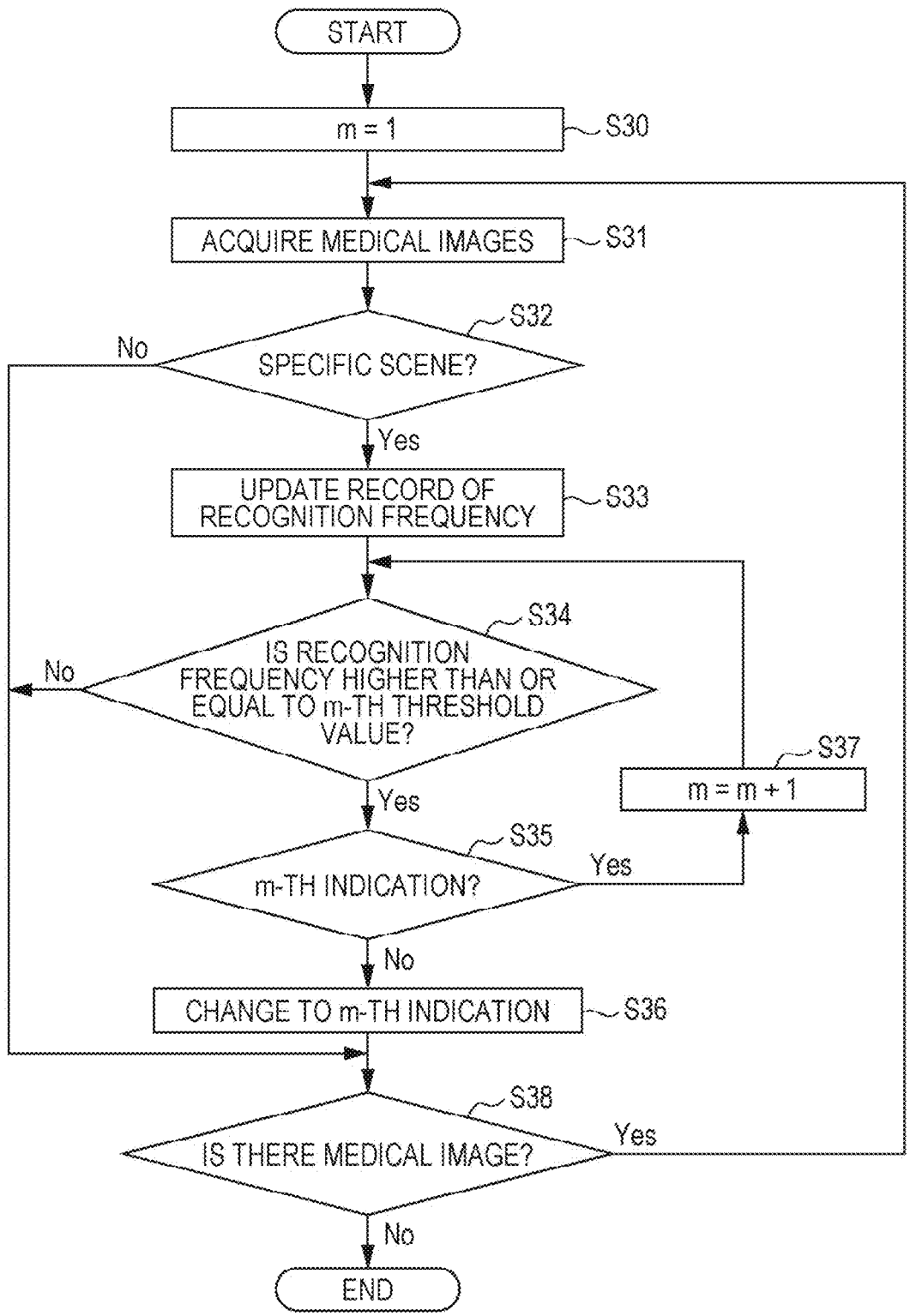
FIG. 9 is a flowchart of a medical image processing method.

FIG. 9 is a flowchart of a medical image processing method in the present modification. In FIG. 9, the value of m represents the number of a screen in a notification indication. A threshold value is set for each of notification indications. Thus, the m-th indication is displayed when the recognition frequency is higher than or equal to the m-th threshold value.

In an initial state, m equals 1 (step S30). The medical image acquiring unit 220 sequentially acquires a plurality of medical images in a chronological manner (step S31). After that, if the specific scene recognizing unit 222 is able to recognize a specific scene in the acquired medical images (Yes in step S32), the frequency acquiring unit 224 updates the record of a recognition frequency (step S33). After that, if the recognition frequency is higher than or equal to the m-th threshold value (Yes in step S34) and if the m-th indication is not yet displayed on the monitor 400 (No in step S35), the display control unit 226 makes a change to the m-th indication (step S36). On the other hand, if the m-th indication is already displayed on the monitor 400, 1 is added to m (step S37).

If the specific scene recognizing unit 222 is unable to recognize a specific scene (No in step S32) or after a change to the m-th indication has been made (step S36), the medical image acquiring unit 220 acquires a subsequent medical image if there is the subsequent medical image (Yes in step S38).

As described above, the present modification is not limited to a change to the first indication and the second indication, and a change to the third or more indication is performed. Accordingly, the user is able to more accurately grasp the recognition frequency of a specific scene in the medical image processing apparatus.

Modification of Update of Recognition Frequency

Next, a modification of update of a recognition frequency will be described. In FIG. 7, a description has been given of the example of updating the recognition frequency on the basis of the number of medical images in which a specific scene has been recognized. In the present modification, the recognition frequency is updated on the basis of the number of chronologically consecutive recognition images. Note that n in the figure represents the number of images in which a specific scene has been recognized, and that N is a frequency update threshold value and is set by a user as appropriate.

Figure 10:
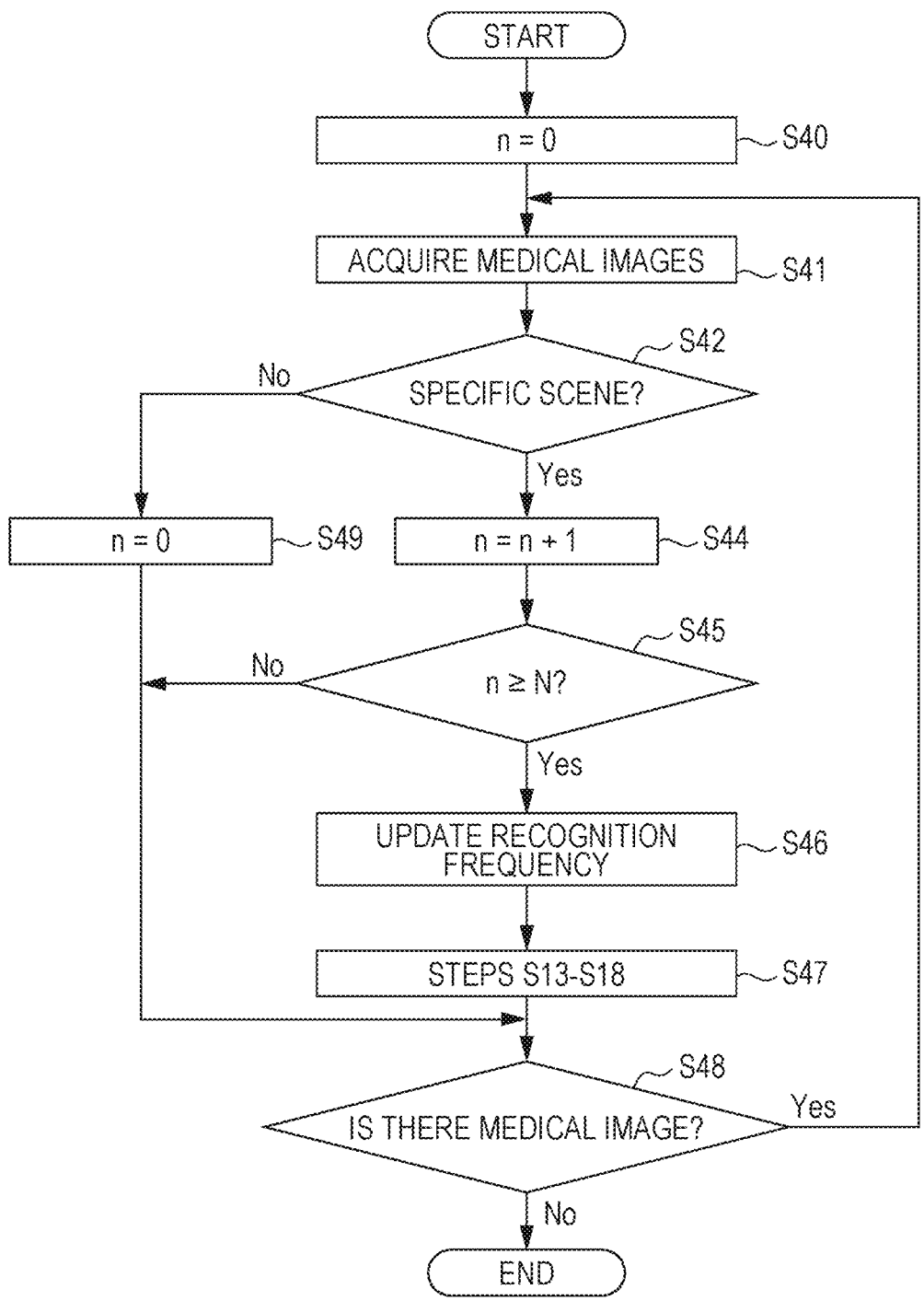
FIG. 10 is a flowchart of acquisition of a recognition frequency.

FIG. 10 is a flowchart of acquisition of a recognition frequency by the frequency acquiring unit 224 in the present modification.

In an initial state, n equals 0 (step S40). The medical image acquiring unit 220 consecutively acquires medical images in a chronological manner (step S41). If the specific scene recognizing unit 222 has recognized a specific scene in a medical image (Yes in step S42), the number of images n in which the specific scene has been recognized is updated to n+1 (step S44). On the other hand, if the specific scene recognizing unit 222 is unable to recognize a specific scene, a counter is set as n=0 (step S49), and a subsequent medical image is acquired if there is the subsequent medical image.

If the updated number of images n in which the specific scene has been recognized is larger than or equal to the frequency threshold value N (Yes in step S45), the recognition frequency is updated (step S46). After that, the display control step described in FIG. 7 (steps S13 to S18: step S47) is performed. After that, if there is a subsequent medical image (Yes in step S48), a process on the subsequent endoscopic image is performed.

As described above, in the present modification, the recognition frequency is updated if a specific scene has been recognized in a predetermined number of consecutive medical images. This makes it possible to output a recognition result of the specific scene recognizing unit 222 by accurately reflecting the observation performed by the user.

Modification 1 of Notification Indication

Next, Modification 1 of a notification indication will be described. In the present modification, a description will be given of various modifications of the case of using a reference image as a notification indication.

FIG. 11 to FIG. 15 are diagrams for describing specific examples of Modification 1-1 to Modification 1-5 of a notification indication. In the figures, IMGB represents an initial indication, IMG1 represents a first indication as a result of switching from the initial indication, and IMG2 represents a second indication as a result of switching from the first indication.

Figure 11:
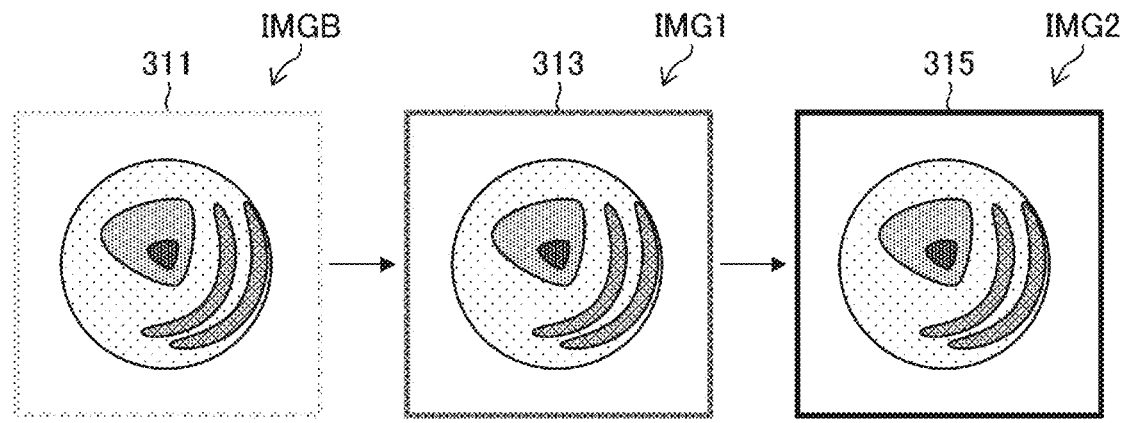
FIG. 11 is a diagram illustrating a specific example of Modification 1-1.

In Modification 1-1 illustrated in FIG. 11, the color of a frame line changes in accordance with the recognition frequency.

For example, a frame line 311 is black in IMGB, a frame line 313 is white in IMG1, and a frame line 315 is red in IMG2. Accordingly, a user viewing the notification indication of the present modification is able to grasp the recognition frequency of the specific scene recognizing unit 222 by the color of the frame line.

Figure 12:
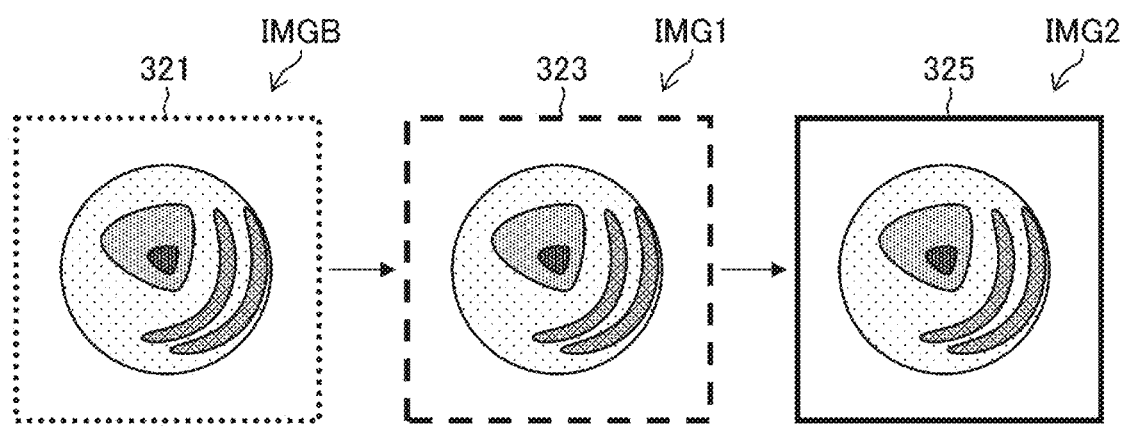
FIG. 12 is a diagram illustrating a specific example of Modification 1-2.

In Modification 1-2 illustrated in FIG. 12, the type of frame line (the type of line) changes in accordance with the recognition frequency.

For example, a frame line 321 is a fine broken line in IMGB, a frame line 323 is a rougher broken line than the frame line 321 in IMG1, and a frame line 325 is a solid line in IMG2. Accordingly, a user viewing the notification indication of the present modification is able to grasp the recognition frequency of the specific scene recognizing unit 222 by the type of frame line.

Figure 13:
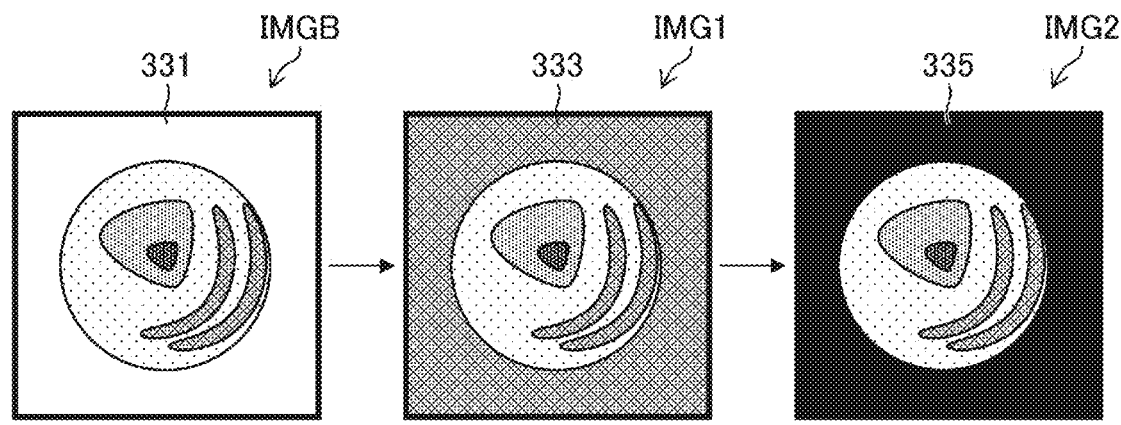
FIG. 13 is a diagram illustrating a specific example of Modification 1-3.

In Modification 1-3 illustrated in FIG. 13, the color of the background of a reference image changes in accordance with the recognition frequency.

For example, a background 331 is white in IMGB, a background 333 is gray in IMG1, and a background 335 is black in IMG2. Accordingly, a user viewing the notification indication of the present modification is able to grasp the recognition frequency of the specific scene recognizing unit 222 by the color of the background.

Figure 14:
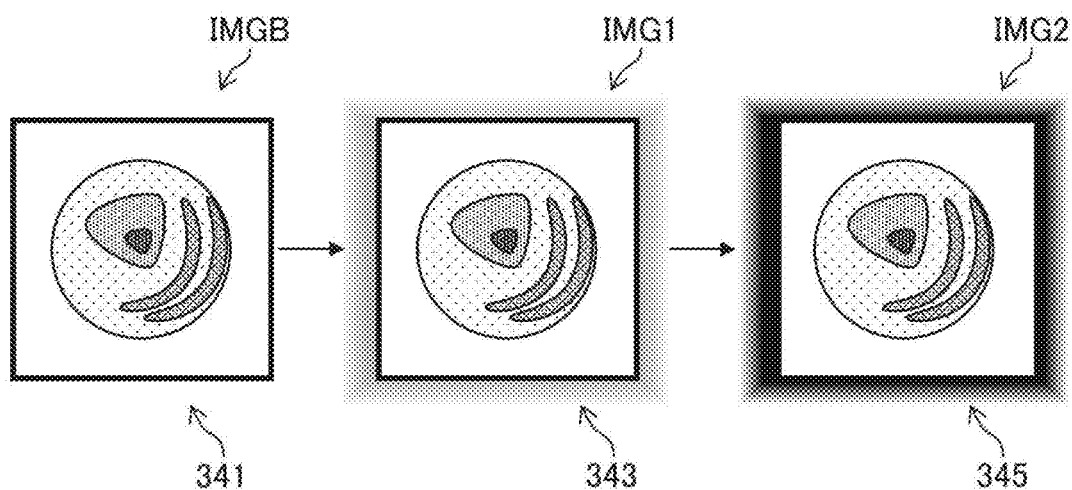
FIG. 14 is a diagram illustrating a specific example of Modification 1-4.

In Modification 1-4 illustrated in FIG. 14, the color of the surrounding region of a reference image changes.

For example, a surrounding region 341 of the reference image is white in IMGB, a surrounding region 343 of the reference image is pink in IMG1, and a surrounding region 345 of the reference image is red in IMG2. Accordingly, a user viewing the notification indication of the present modification is able to grasp the recognition frequency of the specific scene recognizing unit 222 by the color of the surrounding region of the reference image.

Figure 15:
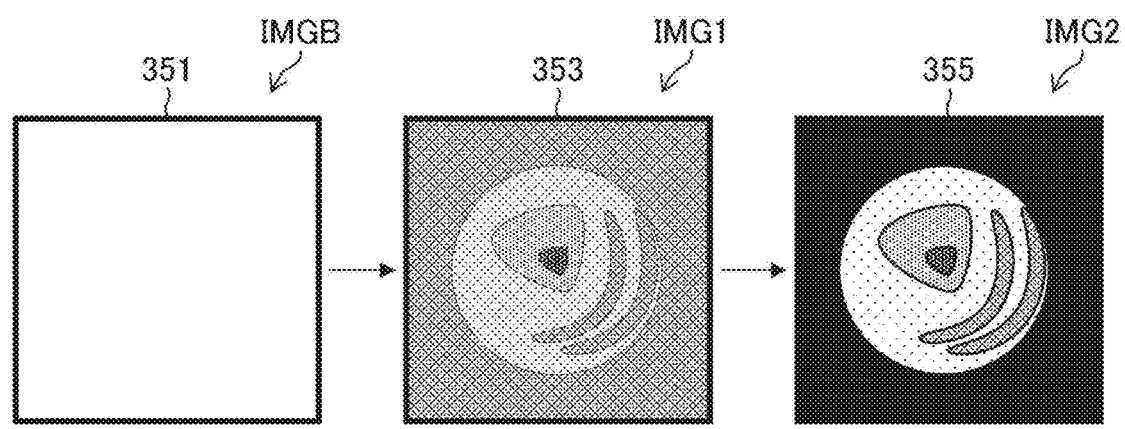
FIG. 15 is a diagram illustrating a specific example of Modification 1-5.

In Modification 1-5 illustrated in FIG. 15, the image of the reference image gradually becomes sharp (the degree of blur changes).

For example, a reference image is not displayed but a plain image 351 is displayed in IMGB, an unsharp (blurred) reference image 353 is displayed in IMG1, and a sharp reference image 355 is displayed in IMG2. Accordingly, a user viewing the notification indication of the present modification is able to grasp the recognition frequency of the specific scene recognizing unit 222 by the degree of sharpness (the degree of blur) of the reference image.

Modification 2 of Notification Indication

Next, Modification 2 of a notification indication will be described. In the present modification, a notification indication is superimposed on a model image including areas corresponding to a plurality of specific scenes.

Figure 16:
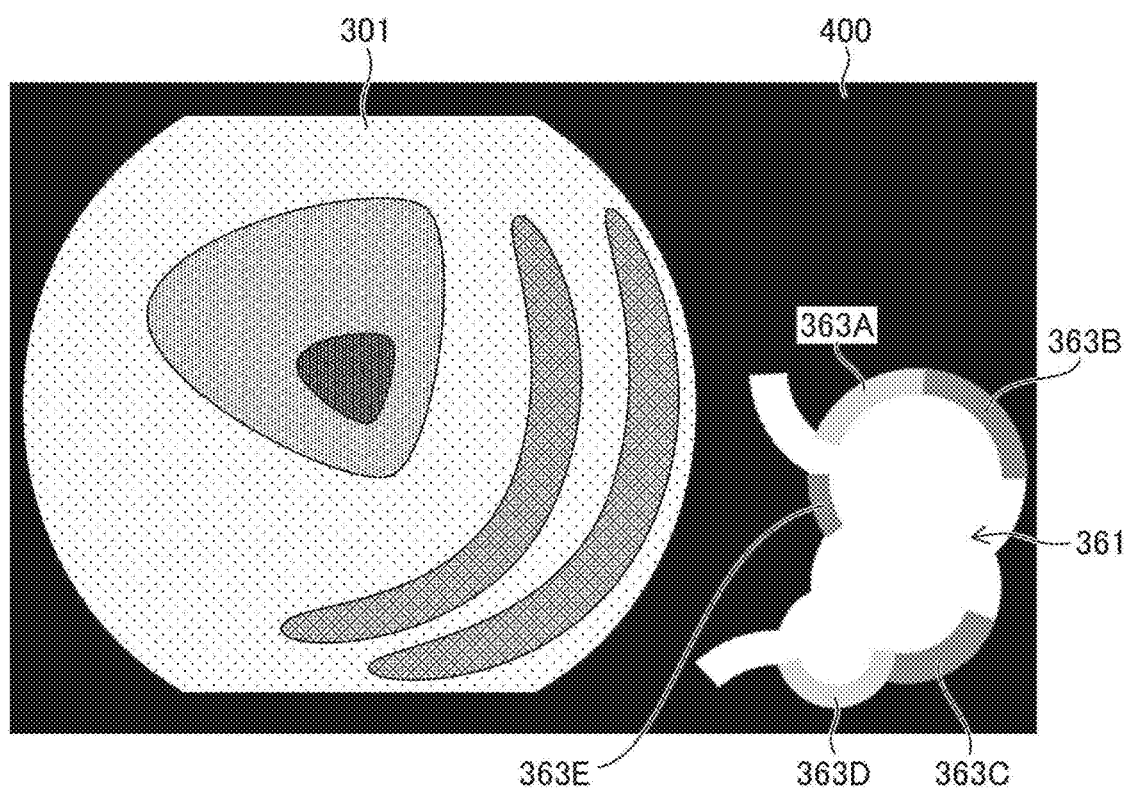
FIG. 16 is a diagram illustrating Modification 2-1.

FIG. 16 is a diagram illustrating Modification 2-1. In the present modification, FIG. 16 is a diagram illustrating a state in which a notification indication is provided on a model image 361 depicting the stomach. The model image 361 includes areas corresponding to a plurality of specific scenes. In a case where the individual specific scenes have been recognized, a band indication with a color that varies according to the recognition frequency is provided as a notification indication. In the case illustrated in FIG. 16, a band indication 363A, which is a first indication for a specific scene A, and a band indication 363D, which is a first indication for a specific scene D, are provided. In addition, a band indication 363B, which is a second indication for a specific scene B, a band indication 363C, which is a second indication for a specific scene C, and a band indication 363E, which is a second indication for a specific scene E, are provided. The band indications 363A and 363D, which are first indications, are displayed in the same color. The band indications 363B, 363C, and 363E, which are second indications, are displayed in the same color. Accordingly, a user viewing the notification indication of the present modification is able to grasp the recognition frequency of the specific scene recognizing unit 222 by the color of the band indication superimposed on the model image.

Figure 17:
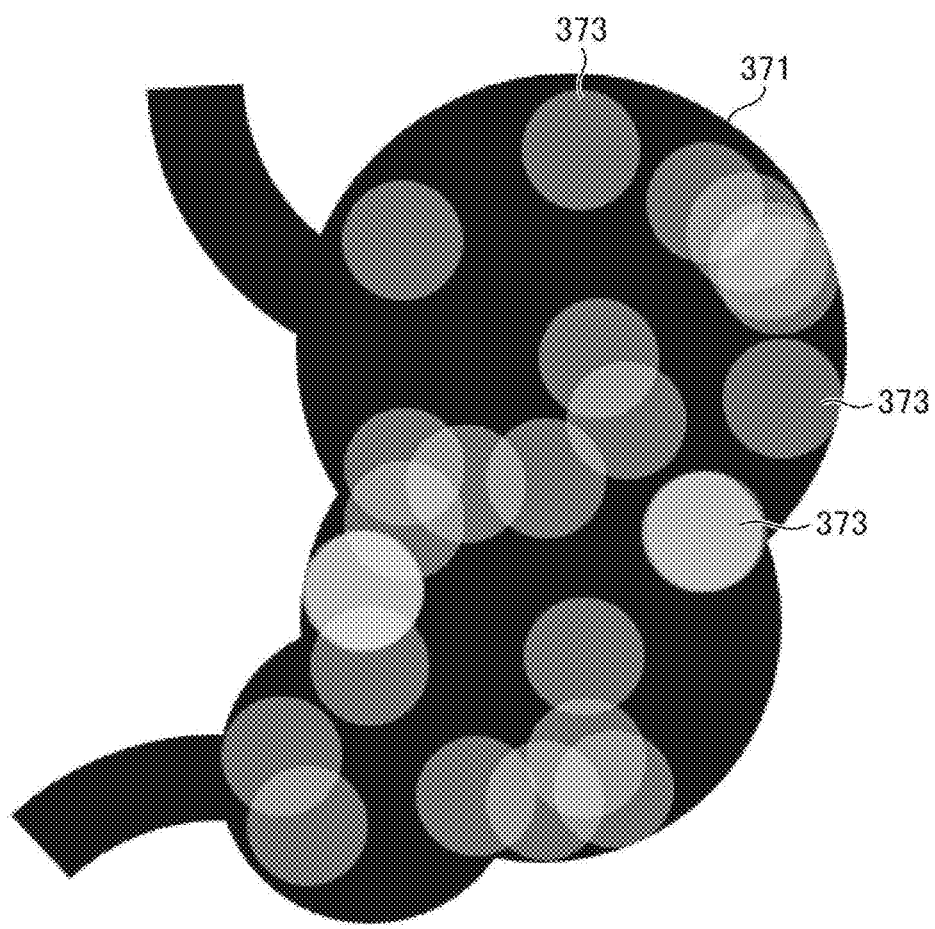
FIG. 17 is a diagram illustrating Modification 2-2.

FIG. 17 is a diagram illustrating Modification 2-2. In the present modification, FIG. 17 is a diagram illustrating a state in which a notification indication is provided on a model image 371 depicting the stomach. The model image 371 includes areas corresponding to a plurality of specific scenes. In a case where each specific scene has been recognized a number of times larger than or equal to a predetermined threshold value, a recognition mark 373 is displayed as a notification indication at the position corresponding to the recognized specific scene. The recognition mark 373 is displayed with an overlap depending on the position of the specific scene. A portion in which recognition marks overlap has a color that varies according to the degree of overlap. As a specific example, the recognition mark 373 is displayed such that the brightness thereof increases as the degree of overlap increases. Accordingly, a user viewing the notification indication of the present modification is able to grasp the recognition frequency of the specific scene recognizing unit 222 by display of the recognition mark 373 displayed on the model image 371 and having a color that changes every time the recognition mark 373 is overlapped.

Modification of Display on Monitor

Next, a modification of display on a monitor will be described. In the present modification, display is performed in two monitors, a first monitor and a second monitor.

Figure 18:
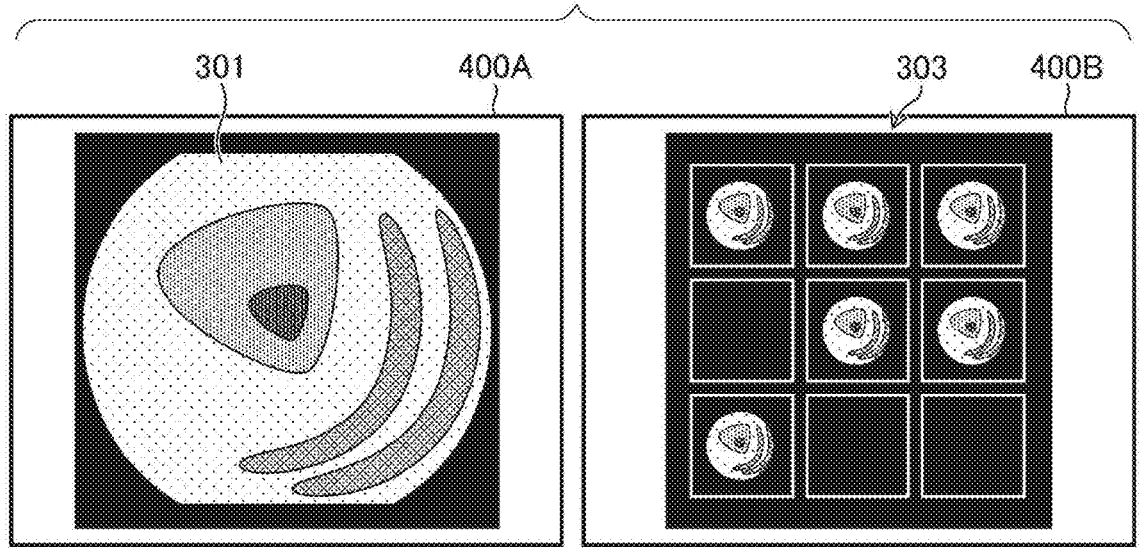
FIG. 18 is a diagram illustrating a case in which display is performed in two monitors.

FIG. 18 is a diagram illustrating a case in which display is performed in two monitors (a first monitor and a second monitor).

On a first monitor 400A, a medical image 301 acquired in real time is displayed. On a second monitor 400B, the notification indication 303, described in FIG. 8, is provided. As a result of providing the notification indication 303 by using the two monitors in this manner, display with an increased visibility can be performed.

Examples of the present invention have been described above. The present invention is not limited to the above-described embodiment, and various modifications can be made without deviating from the spirit of the present invention.

REFERENCE SIGNS LIST

10 endoscope system
100 endoscope
102 handheld operation section
104 insertion section
106 universal cable
108 light guide connector
112 soft part
114 bending part
116 tip rigid part
116A distal-end-side surface
123 illumination unit
123A illumination lens
123B illumination lens
126 forceps port
130 imaging optical system
132 imaging lens
134 imaging element
136 driving circuit
141 air/water supply button
142 suction button
143 function button
144 imaging button
170 light guide
200 endoscope processor apparatus
202 image input controller
204 image processing unit
205 communication control unit
206 video output unit
207 recording unit
208 operation unit
209 audio processing unit
209A speaker
210 CPU
211 ROM
212 RAM
220 medical image acquiring unit
222 specific scene recognizing unit
224 frequency acquiring unit
226 display control unit

What is claimed is:

1. A medical image processing apparatus comprising a processor,
the processor being configured to:
sequentially acquire a plurality of medical images in a chronological manner;
recognize, on the basis of the acquired medical images, a specific scene in the medical images;
acquire a recognition frequency of the recognized specific scene; and
cause a monitor to display, in accordance with the recognition frequency, a notification indication that changes in two or more stages and that indicates a degree of recognition,
wherein the processor is configured to acquire the recognition frequency on the basis of the number of the medical images that are chronologically consecutive of the recognized specific scene, to update the recognition frequency based on a frequency update threshold value and the number of the medical images.

2. The medical image processing apparatus according to claim 1, wherein the processor is configured to cause the monitor to display the notification indication in a color that varies according to the recognition frequency.

3. The medical image processing apparatus according to claim 1, wherein the processor is configured to cause the monitor to display the notification indication with a line type that varies according to the recognition frequency.

4. The medical image processing apparatus according to claim 1, wherein the processor is configured to cause the monitor to display the notification indication at a degree of blur that varies according to the recognition frequency.

5. The medical image processing apparatus according to claim 1, wherein the processor is configured to acquire the recognition frequency on the basis of the number of the medical images of the recognized specific scene.

6. The medical image processing apparatus according to claim 1, wherein the processor is configured to calculate a feature quantity of the medical images of the specific scene and classify the medical images on the basis of the feature quantity of the specific scene, to recognize the specific scene.

7. The medical image processing apparatus according to claim 1, wherein the processor is configured to calculate a feature quantity of the medical images of the specific scene and recognize the specific scene on the basis of a similarity between the feature quantity and the medical images.

8. The medical image processing apparatus according to claim 1, wherein the processor is configured to, in a case where the recognition frequency is higher than or equal to a first threshold value, switch the notification indication from an initial indication to a first indication and cause the monitor to display the first indication.

9. The medical image processing apparatus according to claim 8, wherein the processor is configured to, in a case where the recognition frequency is higher than or equal to a second threshold value larger than the first threshold value, switch the notification indication from the first indication to a second indication and cause the monitor to display the second indication.

10. The medical image processing apparatus according to claim 9, wherein the processor is configured to cause the monitor to display a plurality of reference images each having one of a plurality of the specific scenes, and is configured to provide the first indication and the second indication.

11. The medical image processing apparatus according to claim 9, wherein the processor is configured to cause the monitor to display a model image including areas corresponding to a plurality of the specific scenes, and is configured to provide the first indication and the second indication, with the model image being associated with the specific scenes that have been recognized.

12. The medical image processing apparatus according to claim 11, wherein the processor is configured to cause the monitor to display the notification indication such that the notification indication is superimposed on the model image, with positions at which the specific scenes have been recognized being associated with positions on the model image.

13. The medical image processing apparatus according to claim 1, wherein the processor is configured to, in a case where the specific scene is not yet recognized, cause the monitor to display an initial indication different from the notification indication.

14. A medical image processing method comprising:
a medical image acquisition step of sequentially acquiring a plurality of medical images in a chronological manner;
a specific scene recognition step of recognizing, on the basis of the acquired medical images, a specific scene in the medical images;
a frequency acquisition step of acquiring a recognition frequency of the specific scene recognized in the specific scene recognition step; and
a display control step of causing a monitor to display, in accordance with the recognition frequency, a notification indication that changes in two or more stages and that indicates a degree of recognition,
wherein the method comprises acquiring the recognition frequency on the basis of the number of the medical images that are chronologically consecutive of the recognized specific scene, to update the recognition frequency based on a frequency update threshold value and the number of the medical images.

15. A non-transitory computer-readable tangible recording medium which records thereon a computer instruction that causes, when read by a computer, the computer to execute the medical image processing method according to claim 14.

* * * * *